(12) United States Patent
Bax et al.

(10) Patent No.: US 8,899,125 B2
(45) Date of Patent: Dec. 2, 2014

(54) COUNTERBALANCE ASSEMBLY (75) Inventors: Jeffrey Bax, London (CA); Aaron Fenster, London (CA)

(73) Assignee: Robarts Research Institute, London, Ontario (CA)

( * ) Notice: Subject to any disclaimer, the term of this patent is extended or adjusted under 35 U.S.C. 154(b) by 1079 days.

(21) Appl. No.: 12/680,102

(22) PCT Filed: Sep. 26, 2008

(86) PCT No.: PCT/CA2008/001716
§ 371 (c)(1),
(2), (4) Date: Aug. 20, 2010

(87) PCT Pub. No.: WO2009/039659
PCT Pub. Date: Apr. 2, 2009

(65) Prior Publication Data
US 2010/0319164 A1 Dec. 23, 2010

Related U.S. Application Data (60) Provisional application No. 60/975,514, filed on Sep. 26, 2007.

(51) Int. Cl.
*B25J 18/00* (2006.01)
*B25J 19/00* (2006.01)
*A61B 19/00* (2006.01)

(52) U.S. Cl.
CPC ........ *B25J 19/0016* (2013.01); *A61B 2019/263* (2013.01); *Y10S 901/48* (2013.01)

USPC .............. 74/490.05; 74/567; 16/289; 16/401; 248/292.11; 901/48

(58) Field of Classification Search
USPC ........... 74/54, 523, 490.05, 567; 16/281, 283, 16/284, 286, 289, 401; 901/48; 248/292.11
See application file for complete search history.

(56) References Cited

U.S. PATENT DOCUMENTS

| | | | |
|---|---|---|---|
| 4,277,044 A | 7/1981 | Hamilton | |
| 4,756,204 A | 7/1988 | Wittwer et al. | |
| 4,883,249 A | 11/1989 | Garland | |
| 5,018,700 A | 5/1991 | Hardtke | |
| 5,865,060 A * | 2/1999 | Osborne | 74/49 |
| 5,944,493 A * | 8/1999 | Albertin et al. | 417/273 |
| 7,114,292 B2 * | 10/2006 | Chiang | 49/388 |
| 7,252,277 B2 | 8/2007 | Sweere et al. | |

OTHER PUBLICATIONS

International Search Report completed Nov. 25, 2008 and mailed Jan. 16, 2009 for PCT Int'l Appln. No. PCT/CA2008/001716, filed Sep. 26, 2008, (4 pgs.).

* cited by examiner

*Primary Examiner* — William C Joyce
(74) *Attorney, Agent, or Firm* — Russell T. Manning; Marsh Fischmann & Breyfogle LLP (57) ABSTRACT A mechanical arm assembly comprises an arm rotatable about a pivot, a first force generating device for maintaining the arm at a datum, and a second force generating device for compensating for the first generating device to maintain the arm in positions other than the datum.

27 Claims, 12 Drawing Sheets

Fig 6

COUNTERBALANCE ASSEMBLY

CROSS-REFERENCED TO RELATED APPLICATIONS

This patent application is a U.S. National Stage of PCT/CA2008/001716, filed Sep. 26, 2008, which claims the benefit of U.S. Provisional Application No. 60/975,514, filed Sep. 26, 2007. The entire disclosure of each patent application is hereby incorporated by reference herein.

FIELD OF THE INVENTION

The present invention relates generally to counterbalances and, more particularly, to a counterbalance for a joint of a mechanical arm.

BACKGROUND OF THE INVENTION

Apparatus comprising a mechanical arm that can hold and guide a payload have been shown to be of valuable assistance in various industrial procedures or medical procedures, for example, manipulation of tools, manipulation of cameras or sensors, etc.

These apparatus typically have one or more degrees of freedom and may be manually driven in that the one or more degrees of freedom may be equipped with a brake with motive force being provided by a human user, or may be automated in that at least one degree of freedom is driven by a computer controlled actuator.

A balancing mechanism may be used to counteract the force of gravity for hinged and/or articulated arm. Elimination or reduction of the effects of gravity allow the use of smaller power sources, gears and/or less effort exerted by a manual user. This is desirable from a cost standpoint and allows for a more compact design which, in turn, allows greater accessibility to the workspace.

Several counterbalancing mechanisms have been previously disclosed, for example, U.S. Pat. No. 4,756,204, U.S. Pat. No. 4,546,233, or U.S. Pat. No. 4,500,251.

Balancing mechanisms used on articulated arms and hinge mechanisms include counterweights. However, the use of counterweights can result in added mass and increase in arm inertia.

A tension spring or passive pneumatic balancer may be used for balancing within a small angle or within a single quadrant (i.e. from a horizontal to vertically upward orientation). However, conventional tension springs typically do not adequately balance the gravitational load. Also, it is inherent in most spring balancing methods that complete balance is possible only for one or two configurations of the arm and spring combination. As the robot arm moves away from that configuration in either of two possible directions, an unbalance is generated. Thus, a danger of this mechanism may be drifting or falling under the force of gravity when actuation is removed or reduced. Therefore, such mechanisms are usually provided with brakes to alleviate the potential danger, or are overbalanced against gravity.

Compression springs operating on small moment arms may overcome an angular limitation problem and offer better balance over the entire range of travel of the robot's arm. However, the problem of drift or falling under gravity also exists with compression springs.

It is an object of an aspect of the present invention to provide a counterbalance assembly for a joint of a mechanical arm.

SUMMARY OF THE INVENTION

In an aspect, there is provided a counterbalance assembly for a joint of a mechanical arm comprising:
a first force generating device;
a second force generating device;
the first and second force generating devices interacting with at least first and second cams, respectively;
the first and second cams fixed eccentrically relative to the pivot of a joint;
and the relationship of the first spring to the second spring and the first cam to the second cam being preserved throughout rotation of the joint.

In another aspect, there is provided a mechanical arm assembly comprising:
an arm rotatable about a pivot,
a first force generating device for maintaining the arm at a datum,
a second force generating device for compensating for the first generating device to maintain the arm in positions other than the datum.

BRIEF DESCRIPTION OF THE DRAWINGS

Embodiments will now be described, by way of example only, with reference to the attached Figures, wherein:

FIG. 2a illustrates a cross-sectional view of a dual spring counterbalance assembly showing springs coupled to cams set eccentrically relative to a pivot of a joint;

FIG. 2b is a schematic diagram illustrating the geometric relationship between each spring-cam assembly shown in FIG. 2a;

DETAILED DESCRIPTION

Figure 1A:
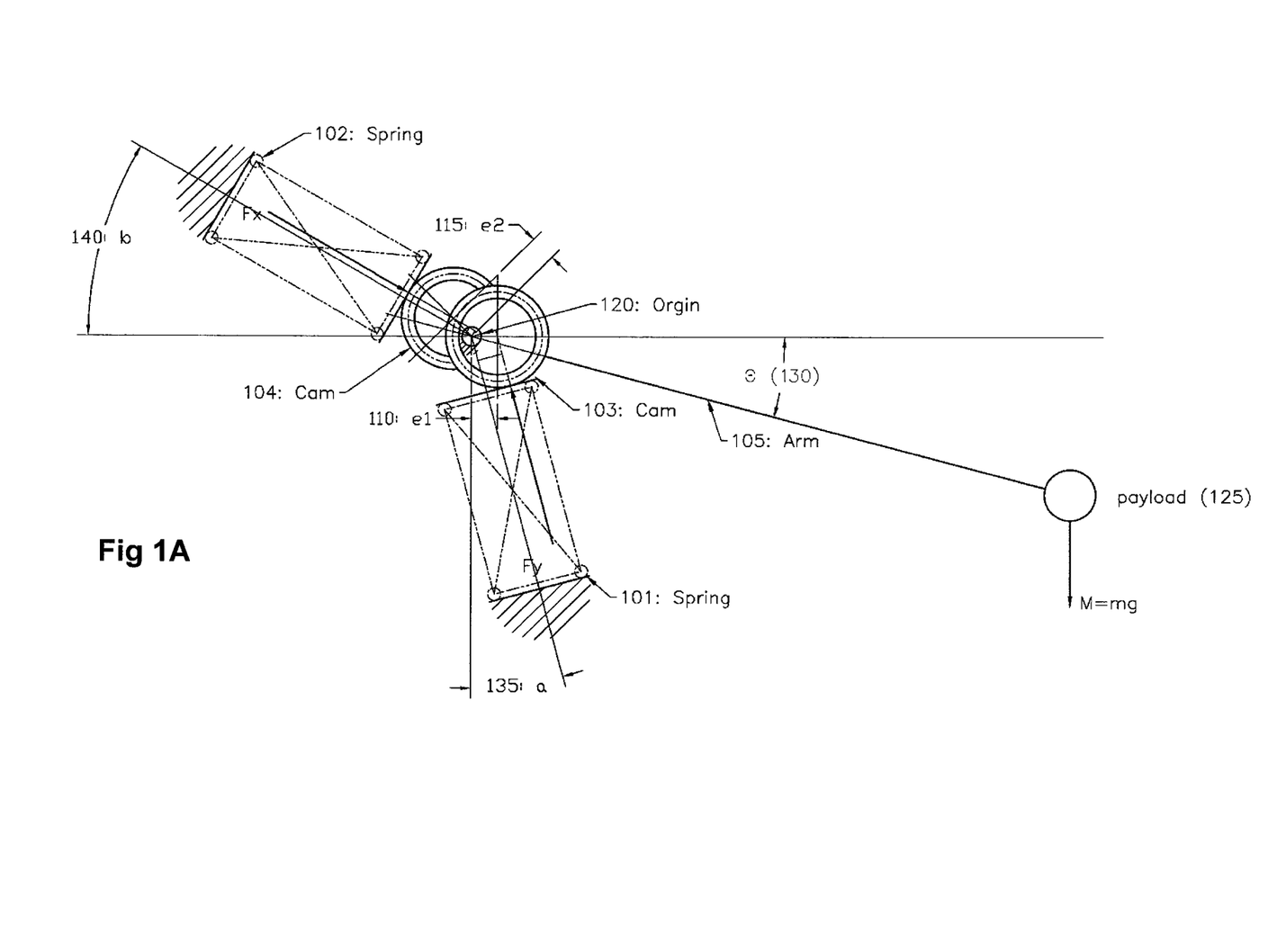
FIG. 1a illustrates a dual spring counterbalance assembly at a joint of a mechanical arm using springs that are fixed to a ground and cams set eccentrically relative to the pivot of the joint.
Figure 1B:
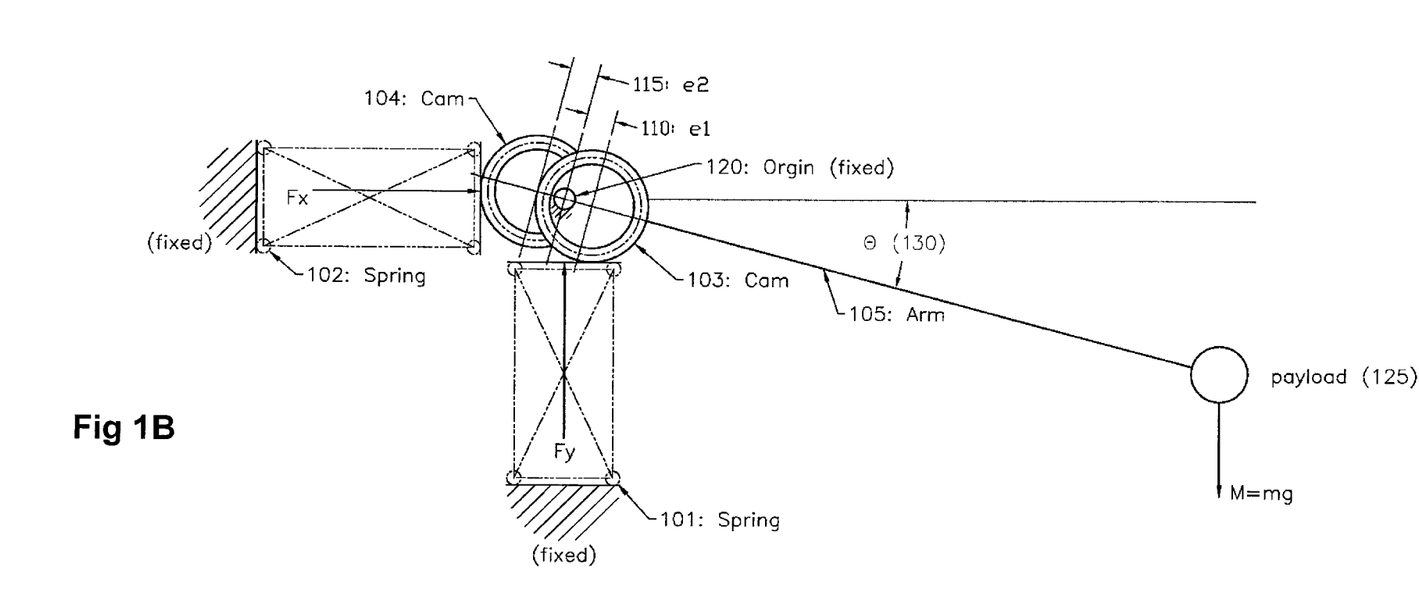
FIG. 1b illustrates a variant of the counterbalance assembly shown in FIG. 1a with a different orientation of springs and cams.

FIGS. 1a to 1e are schematic illustrations of spring counterbalance assemblies which show the geometric relationship of spring and cams. Referring to FIGS. 1a and 1b, the spring counterbalance assembly comprises two compression springs (101, 102), each of which are fixed at the base (or grounded fixture) and the other end(s) are connected to eccentric circular cams (103, 104) by a yoke (not shown), such that each cam is free to rotate about the fulcrum or pivot (120) of a joint, and the springs are free to compress (or stretch). The springs may be adjustable. Cam 103 is eccentrically set relative to the pivot (120) of a joint by a distance equal to e1 (110), and cam 104 is eccentrically set relative to the pivot (120) of the joint by a distance of e2 (115).

Spring (101) interacts only with cam (103), and spring (102) interacts with cam (104). Both of the cams are in turn pinned to the lever/arm (105) that supports the payload (125). The compressive (or tensile) force exerted by each spring results in a net torque being exerted about the pivot (120) of the lever supporting the load.

FIGS. 1a and 1b schematically illustrate different orientations of springs and cams in a counterbalance assembly designed to fully support the weight of a payload about a hinged connection which is connected to a ground or stable fixture. The base of each spring is anchored to the ground (or fixture) while the lever/arm (105), pinned to the cams (103, 104) is free to rotate about the pivot (120) of a joint of a mechanical arm. The ability to establish equilibrium of torque relative to pivot (120) is not limited to specific spring-cam orientations shown in FIGS. 1a and 1b as will be apparent from equilibrium equations provided below.

In FIG. 1a the relationship between spring (101) and cam (103) to the lever/arm supporting the load is orientated such that the line joining the pivot (120) and e1 (110) is not coincident with the line joining the pivot (120) to the center of gravity of the payload (125), which includes mass of the lever/arm (105). In an example of an alternate orientation shown in FIG. 1b the relationship between spring (101) and cam (103) to the lever/arm supporting the load is orientated such that the line joining the pivot (120) and e1 (110) is coincident with the line joining the pivot (120) to the center of gravity of the payload (125), which includes mass of the lever/arm (105). In both FIGS. 1a and 1b the orientation of the spring/cam relationship is preserved throughout rotation. Thus, if the cam is in a desired position with respect to the pivot, that will define the orientation of the spring in space. If the spring is in a desired position in space, that will define the position of the cam with respect to the pivot.

In the configuration shown in FIG. 1b, the orientation of the cam to the lever/arm constrains spring (101) to a vertical position. If the eccentric point is in between the pivot/fulcrum and center of gravity as shown in FIG. 1b, spring (101) will exert a compressive force in its current configuration to offset the payload when the arm is horizontal (theta (130)=0 degrees). If the pivot/fulcrum is in between eccentric point and center of gravity (not shown), spring (101) will exert a tensile force to offset the weight of the payload. The user can initially set spring (101) such that its initial compression offsets the mass of the payload, for example when the arm is in the horizontal position (ie, when the cam 103 is 90 degrees out of phase with spring 101). The pre-compression of spring (101) will typically be set with the arm (105) in the horizontal position since the torque exerted by the arm is greatest at this point. However, pre-compression may also be set with the arm being above or below horizontal by extrapolation.

In FIG. 1b, the relationship between spring (102) and cam (104) to the lever/arm supporting the load is orientated such that the line joining the pivot (120) and e1 (10) is coincident with the line joining the pivot (120) to the center of gravity of the payload (125), which includes mass of the lever/arm (105). The orientation of the cam to the lever constrains spring (102) to a horizontal position. If the eccentric point is in between the pivot and center of gravity (not shown), spring (102) will exert a tensile force in its current configuration to offset the linear change in force of spring (101). If the pivot (120) is in between eccentric point and center of gravity as shown in FIG. 1b, spring (102) will exert a compressive force. In the specific example shown in FIG. 1b, spring (102) is not adjustable, and is set by design such that the spring exerts no load on cam (104) when the arm (105) is in a vertical orientation (90 or 270 degrees relative to a Cartesian coordinate system where 0 degree corresponds to the positive X axis).

Still referring to FIG. 1b, the relationship between each cam-spring pair is such that each cam is 180 degrees out of phase with each other (pivot (120) is in-between the eccentric points (110) and (115)). In this configuration, each of the springs is constrained to be 90 degrees out of phase with each other (perpendicular). The relationship created from the constrained relationship between each spring/cam pair is the torque exerted by spring (101) leads spring (102) by 90 degrees.

In an alternate embodiment, each spring/cam pair can be rotated about the pivot (120) to any position (for example, springs are aligned, 0 or 180 degrees) as long as the relationship between the cam and corresponding spring is maintained.

Thus, the ability to establish equilibrium relative to pivot (120) is not limited to specific spring-cam orientations shown in FIGS. 1a and 1b as will also be apparent from equilibrium equations provided in the following paragraphs.

Figure 1C:
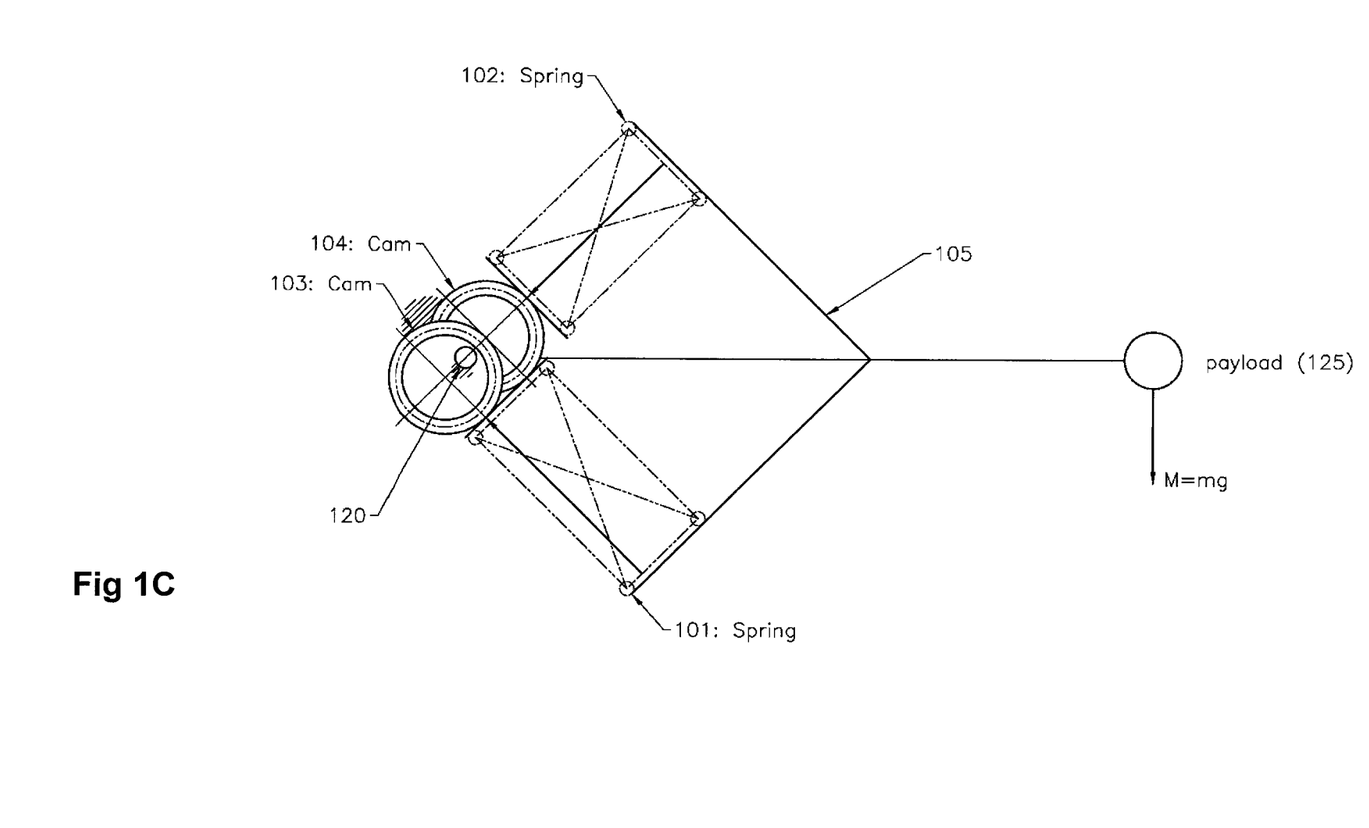
FIG. 1c illustrates a dual spring counterbalance assembly having springs attached to the payload arm.
Figure 1D:
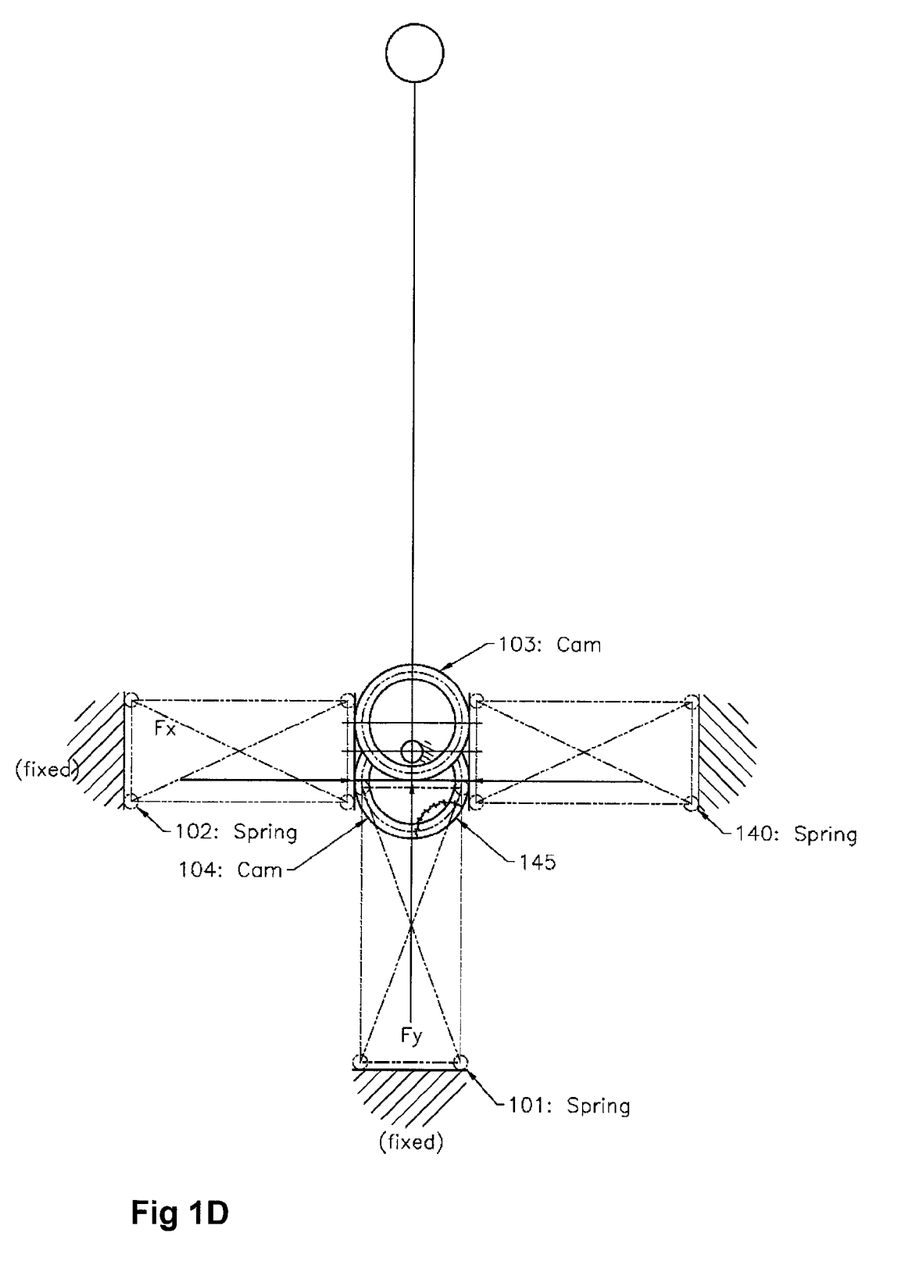
FIG. 1d illustrates a triple spring counterbalance assembly with an additional spring and an additional cam being added to the counterbalance assembly shown in FIG. 1b.
Figure 1E:
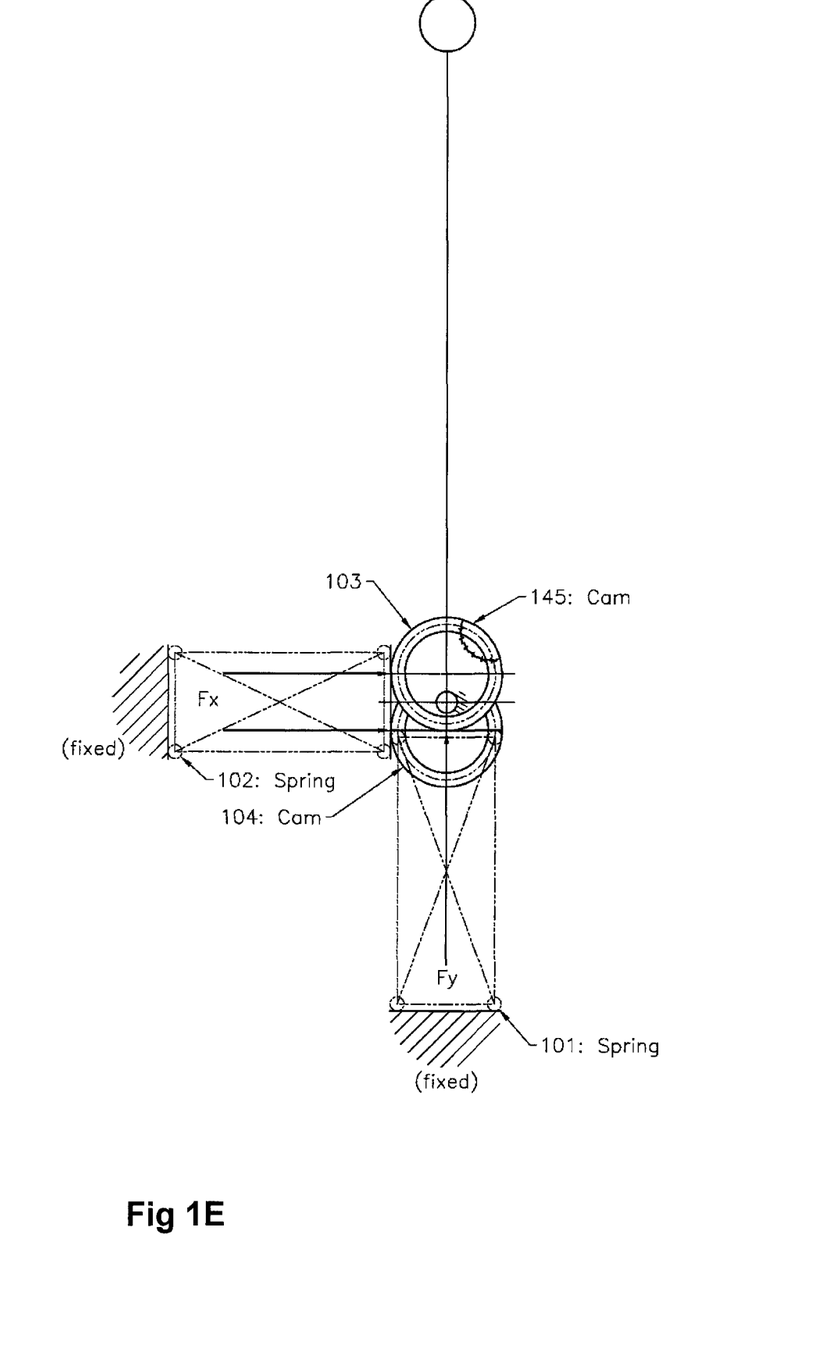
FIG. 1e illustrates a simplified variant of the counterbalance assembly shown in FIG. 1d with removal of a spring resulting in two springs interacting with three cams.
Figure 1F:
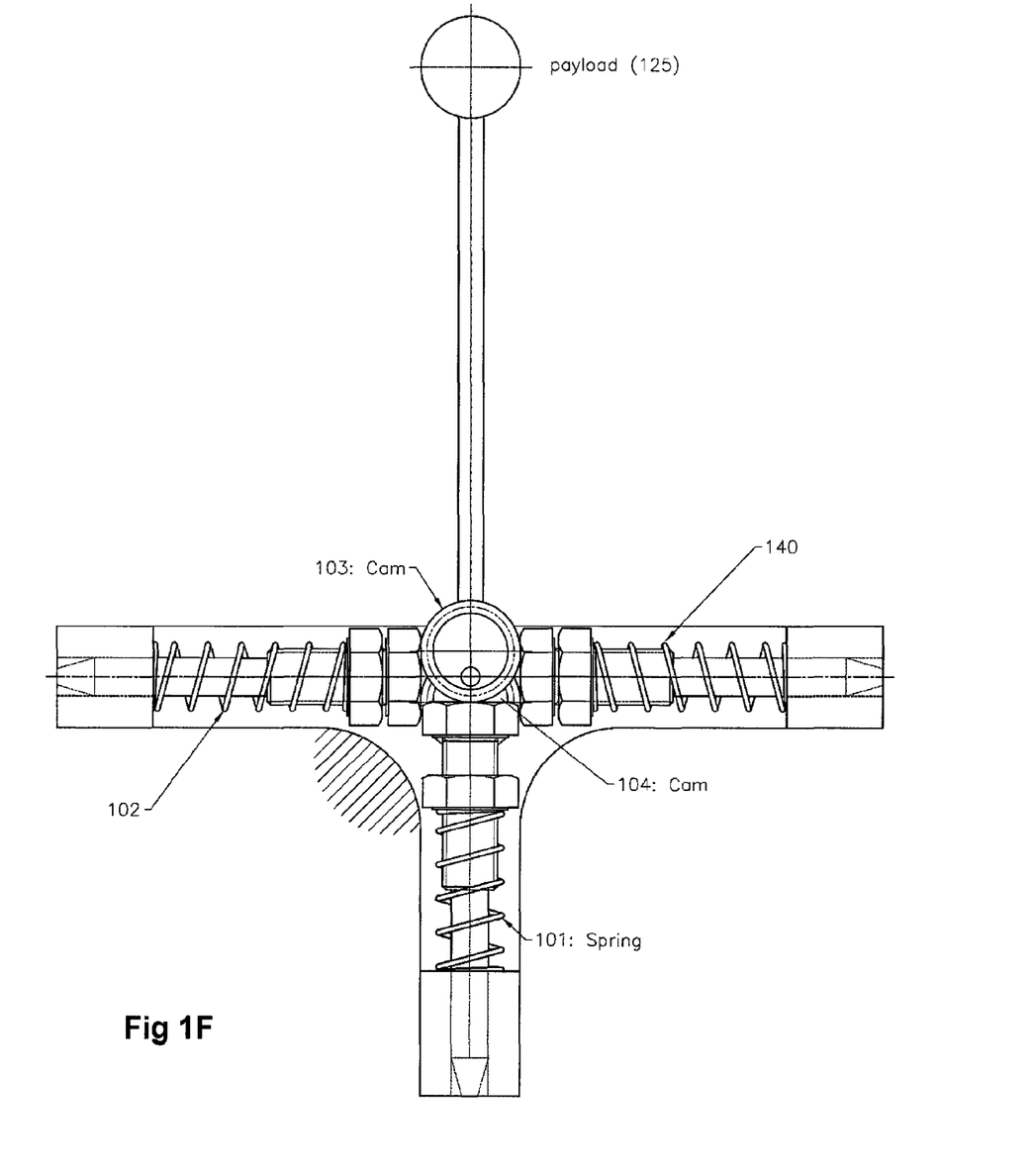
FIG. 1f illustrates a mechanical arm of the counterbalance assembly shown in FIG. 1d; spring/cam relationship in a spring balance mechanism for a mechanical arm.
Figure 1G:
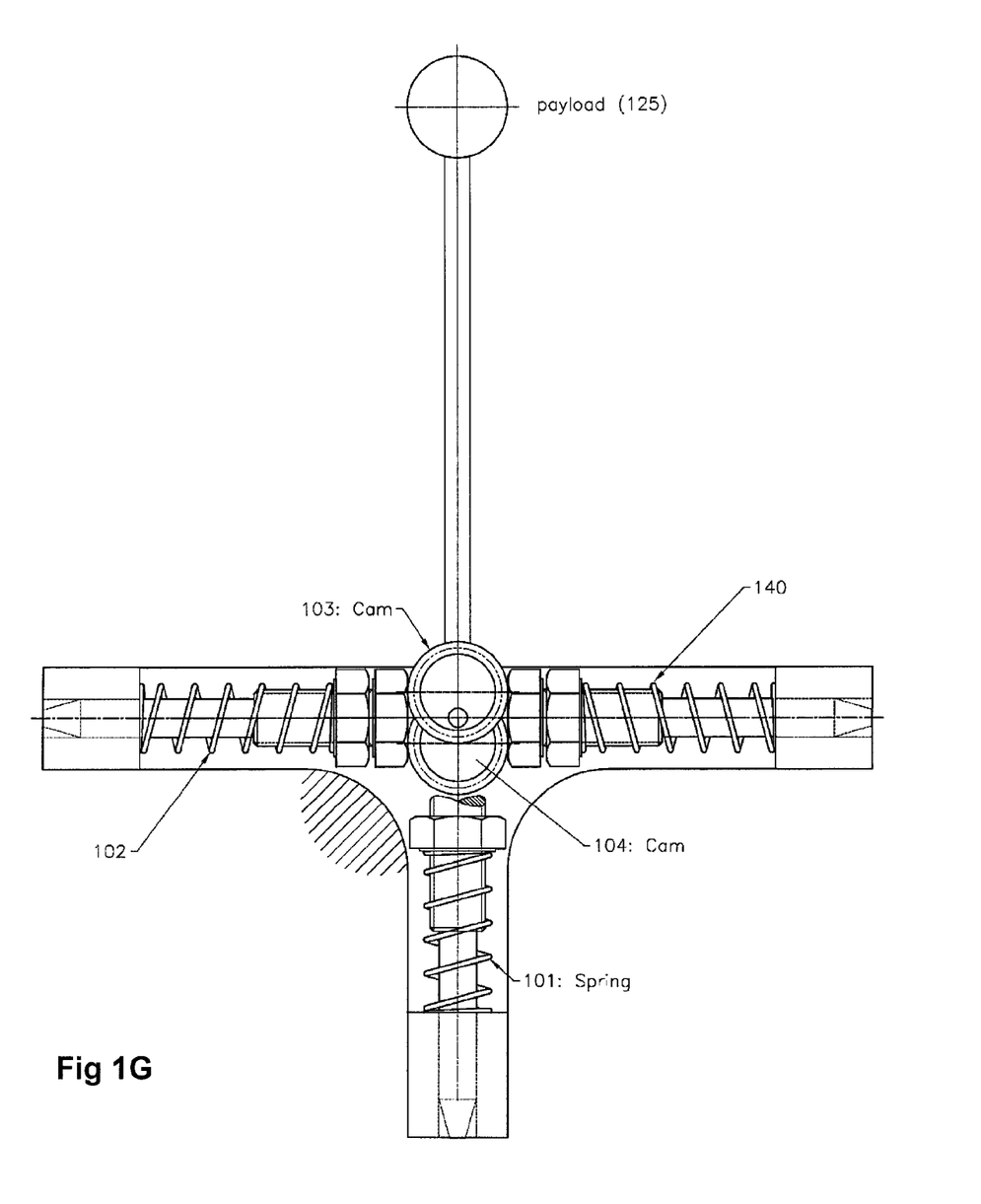
FIG. 1g is the same as FIG. 1f except that the bolt head extension of a spring is cut away to more clearly show two cams.

Alternatives to FIGS. 1a and 1b are shown in FIGS. 1c-1e. FIG. 1c is an alternate embodiment of the mechanism illustrated in FIGS. 1a and 1b where the springs are attached to the arm (105) and the cams are attached to the ground (or fixture). FIG. 1d adds an additional spring (140) and cam (145) to the spring/cam relationships shown in FIGS. 1a and 1b and thus eliminates the need for spring (102) to exert both compressive and tensile loads. Spring (102) as shown in FIGS. 1a and 1b when coupled by a yoke to cam (104) can be required to exert both tensile and compressive loads. Addition of spring (140) and cam (145) shown under the cutaway portion of cam (104) in FIG. 1d, allows the use of compression springs (102 and 140) that abut their respective cams (104 and 145) and exert only compressive loads. FIG. 1e shows a further simplification of the assembly illustrated in FIG. 1d with spring 102 interacting with both cams (145 and 104). Cam 145 is shown under the cutaway of cam (103). The assembly design shown in FIG. 1d allows for the use of compression spring (102) to abut cams and only exert a compressive load, while removing the need for spring (140). The assembly shown in FIG. 1e can be even further simplified by setting spring (102) to interact with both cams (103 and 104), thus removing the need for spring (140) and cam (145). FIGS. 1f and 1g show the assembly design of FIG. 1d as implemented on a mechanical arm.

The following is a description of the equilibrium equations that govern the geometric spring/cam relationships shown in FIG. 1a-1e. The force friction has been omitted from this analysis as it has no bearing on the equilibrium equations when the machine is at rest. Friction can be used as an advantage to construct inexpensive mechanisms that behave in a similar manner to the case illustrated in FIG. 1 but do not fully balance the load. The sum of all the frictional forces between every moving part within the mechanism would prevent drift.

Referring to FIG. 1a, equilibrium about the pivot (120) is established when the net torque is zero, i.e.:

$$T_g + T_x + T_y = 0 \tag{1},$$

where Tg is the unbalanced torque due to the payload (125), and the unbalanced torque produced from spring (101) and (102) are Tx and Ty respectively. The unbalanced torque produced by the weight is the product of the gravitational force due to the payload M, and the shortest distance between the force vector (M=mg) and the point (120):

$$T_g = Mr\cos(\theta) \qquad (2).$$

The net torque of spring (101) about (120) is equal to the sum of the torque produced from the compression of the spring due to the arm displacement (130) and the pre-compression of the spring when the arm is horizontal (130: $\theta=0$), and is given by:

$$T_y = -(K_y e_1 \sin(\theta) + K_y \Delta y)(e_1 \cos(\theta)) \qquad (3),$$

where Ky is the spring rate of (101), and $\Delta y$ is the displacement of the spring from rest when the arm is horizontal. The net torque produced from spring (102) is given by:

$$T_x = K_x e_2^2 \cos(\theta)\sin(\theta) \qquad (4),$$

where Kx is the spring rate of (102) and is uncompressed when the arm is in a vertical orientation (up or down). Substituting equations (2-4) into 1 gives the following:

$$Mr\cos(\theta) - K_y \Delta y e_1 \cos(\theta) + K_x e_2^2 \cos(\theta)\sin(\theta) - K_y e_1^2 \sin(\theta)\cos(\theta) = 0 \qquad (5).$$

Equation 5 is equal to zero and independent of the angle $\theta$, and the spring-cam orientations (135: a) and (140: b) under the following conditions:

$$Mr = K_y \Delta y e_1 \qquad (6),$$

$$K_x e_2^2 = K_y e_1^2 \qquad (7).$$

Equation 6 provides that spring (101) pre-compression is set to counterbalance the payload (125) at the arm position within the desired rotation where the torque exerted is greatest, typically when the arm is horizontal. Equation 7 provides the physical constraints which govern the relationship of each spring cam pair.

Equation 5 can be expanded and written in the following form:

$$Mr\cos(\theta) - (K_{ya}\Delta y_a e_{1a} + K_{yb}\Delta y_b e_{1b} + \ldots)\cos(\theta) + (K_{xa}e_{2a}^2 + K_{xb}e_{2b}^2 + \ldots)\cos(\theta)\sin(\theta) - (K_{ya}e_{1a}^2 + K_{yb}e_{1b}^2 + \ldots)\sin(\theta)\cos(\theta) = 0 \qquad (8).$$

Equation 8 is equal to zero and independent of the angle $\theta$, and the spring-cam orientations (a:135) and (b:140) under the following conditions:

$$Mr = K_{ya}\Delta y_a e_{1a} + K_{yb}\Delta y_b e_{1b} + \ldots \qquad (9),$$

$$K_{xa}e_{2a}^2 + K_{xb}e_{2b}^2 + \ldots = K_{ya}e_{1a}^2 + K_{yb}e_{1b}^2 + \ldots \qquad (10).$$

From equations 9 and 10, the following illustrative embodiments are apparent:

- The spring (101), and cam (103) can be replaced with multiple spring and cam assemblies.
- If ($e_{1a}^2 = e_{1b}^2 = \ldots$), and ($K_{ya} = K_{yb} = \ldots$) then the spring (101) can be replaced by multiple springs acting against the cam (103).
- The spring (102), and cam (104) can be replaced with multiple spring and cam assemblies.
- If ($e_{2a}^2 = e_{2b}^2 = \ldots$), and ($K_{xa} = K_{xb} = \ldots$) then the spring (102) can be replaced by multiple springs acting against the cam (104).
- If multiple springs are used in place of (101), then each spring can be preloaded a different amount to offset the payload when the arm is horizontal.

Now referring to FIG. 1c, an alternate embodiment of the mechanism illustrated in FIGS. 1a and 1b is shown where the springs are attached to the arm (105) and the cams are attached to the ground (or fixture). Consistent with the embodiments shown in FIGS. 1a and 1b, in FIG. 1c equilibrium about the pivot (120) is established when the net torque is zero, i.e.:

$$T_g + T_x + T_y = 0 \qquad (1),$$

where Tg is the unbalanced torque due to the payload (125), and the unbalanced torque produced from spring (101) and (102) are Tx and Ty respectively. The unbalanced torque produced by the weight is the product of the gravitational force due to the payload M, and the shortest distance between the force vector (M=mg) and the point (120):

$$T_g = Mr\cos(\theta) \qquad (2).$$

The net torque of spring (101) about (120) is equal to the sum of the torque produced from the compression of the spring due to the arm displacement (130) and the pre-compression of the spring when the arm is horizontal (130: $\theta=0$), and is given by:

$$T_y = (K_y e_1 \sin(\theta + \pi) + K_y \Delta_y)(e_1 \cos(\theta + \pi)), \qquad (11a)$$

$$= (-K_y e_1 \sin(\theta) + K_y \Delta_y)(-e_1 \cos(\theta)), \qquad (11b)$$

where Ky is the spring rate of (101), and $\Delta y$ is the displacement of the spring from rest when the arm is horizontal. This spring force is equal and opposite of the spring in FIG. 1a, and the cams are 180 degrees out of phase to the cam arrangement in FIG. 1a.

The net torque produced from spring (102) is given by:

$$T_x = -K_x e_2^2 \cos(\theta + \pi)\sin(\theta + \pi) \qquad (12a),$$

$$T_x = -K_x e_2^2 \cos(\theta)\sin(\theta) \qquad (12b),$$

where Kx is the spring rate of (102) and is uncompressed when the arm is in a vertical orientation (up or down). Substituting equations (2), (11) and (12) into (1) gives the following:

$$Mr\cos(\theta) - K_y \Delta y e_1 \cos(\theta) - K_x e_2^2 \cos(\theta)\sin(\theta) + K_y e_1^2 \sin(\theta)\cos(\theta) = 0 \qquad (13).$$

Equation (13) is equivalent to equation (5).

In FIGS. 1a-1e when the illustrated mechanism is in balance, the torque exerted by the payload is equal and opposite to the torque exerted by the springs, regardless of the angular orientation of the arm (105). As illustrated in equation (7), this condition is met when the product of e1 squared and Ky is equal to the product of e2 squared and Kx. If e1 and e2 are equal, then both springs must have the same spring rate (Kx=Ky).

If tension springs are used in place of compression springs in FIG. 1a, then placing the payload on the opposite side of the pivot (or rotating both cams 180 degrees), equilibrium about the pivot (120) is established when the net torque is zero, i.e.:

$$-T_g - T_x - T_y = 0 \qquad (1),$$

where $-T_g$ is the unbalanced torque due to the payload (125), on the opposite side of the fulcrum illustrated in FIG. 1a, and the unbalanced torque produced from tension spring (101) and (102) are $-Tx$ and $-Ty$ respectively. The unbalanced torque produced by the weight is the product of the gravitational force due to the payload M, and the shortest distance between the vector (M) and the point (120):

$$-T_g = -Mr\cos(\theta) \qquad (2).$$

The net torque of spring (101) about (120) is equal to the sum of the torque produced from the extension of the spring due to the arm displacement (130) and the pre-tension of the spring when the arm is horizontal (130: θ=0), and is given by:

$$T_y = +(K_y e_1 \sin(\theta) + K_y \Delta y)(e_1 \cos(\theta)) \quad (3),$$

where Ky is the spring rate of (101), and Δy is the displacement of the spring from rest when the arm is horizontal. The net torque produced from spring (102) is given by:

$$T_x = -K_x e_2^2 \cos(\theta) \sin(\theta) \quad (4),$$

where Kx is the spring rate of (102) and is uncompressed when the arm is in a vertical orientation (up or down). Substituting equations (2-4) into 1 gives the following:

$$-Mr \cos(\theta) + K_y \Delta y e_1 \cos(\theta) - K_x e_2^2 \cos(\theta) \sin(\theta) + K_y e_1^2 \sin(\theta) \cos(\theta) = 0 \quad (5).$$

Figures 2A, 2B:
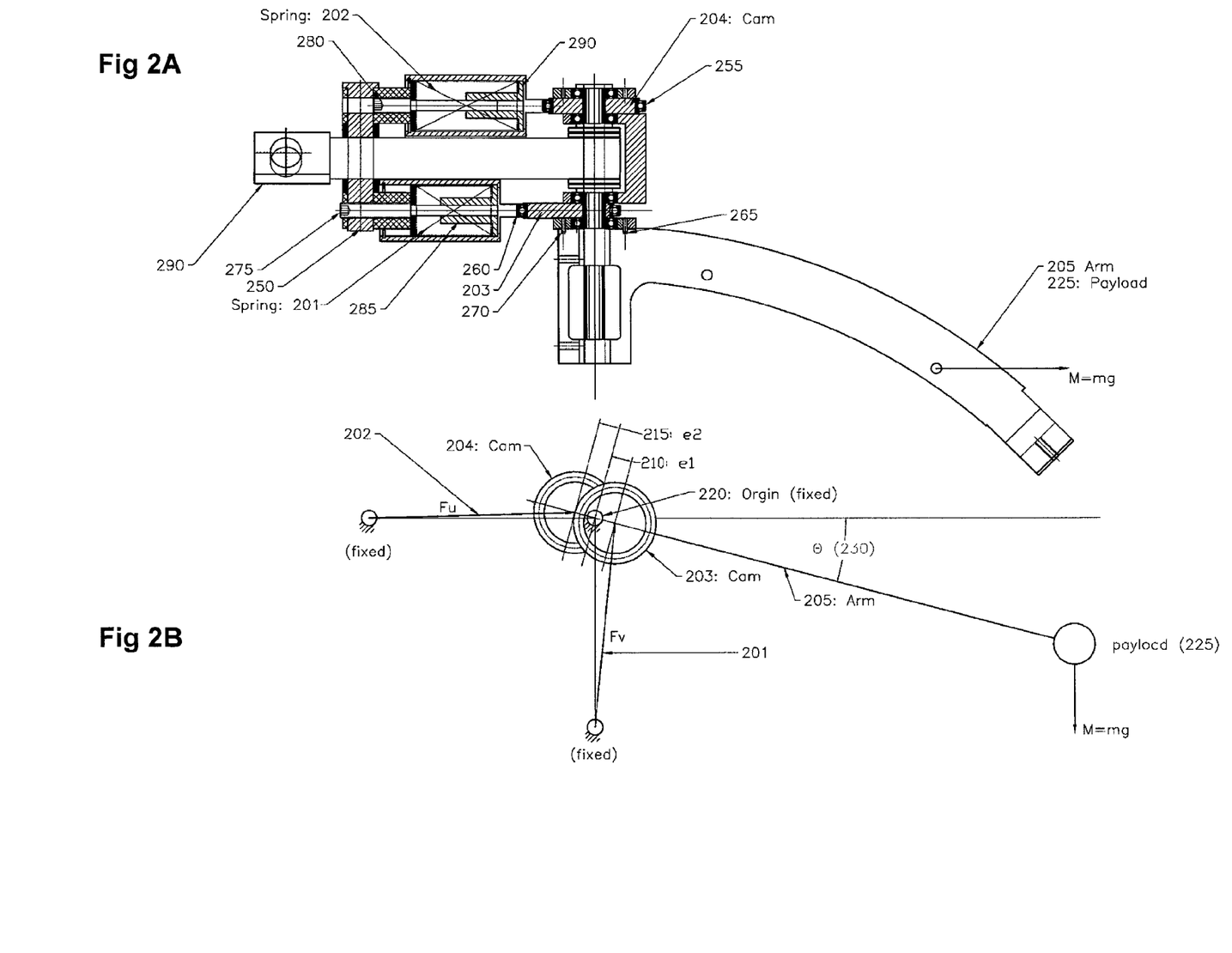

Since this is equation 5, then it becomes apparent that tension springs can be used as a replacement for compression springs Now referring to FIG. 2a, an alternate embodiment is illustrated, where both of the compression springs are pivotally attached (250) at the base (or grounded fixture) and the other ends are fixed to the cams by a hinged connection (roller bearings 255 and 260). This mechanism exerts its torque through the pins (265) and (270) to the arm (205) supporting the payload (225).

The section view of this assembly illustrates that spring (201) and (202) can only exert compressive loads on the cams. Spring (201) is compressed between the adjustment screw (275) attached to the base (290) and the bushing (285), resulting in a compressive load on cam (203). Spring (202) is compressed in a similar manner between adjustment screw (280) and bushing (290) to exert compressive loads on cam (204). As a result this variation is capable of fully supporting the weight of the payload to a maximum of ±90 degrees from its rest position. The rest position of the arm is in the horizontal position (not shown in FIG. 2a).

Adjustment screw (275) is used to set the pre-compression load on spring (201) to support the weight of the payload when the arm is in the horizontal position (preload=Mr). Adjustment screw is set such that the spring (202) exerts no load on cam (204) when the arm (205) is in a vertical orientation (illustrated in FIG. 2a).

FIG. 2b is a schematic diagram illustrating the geometric relationship between each spring/cam pair shown in FIG. 2a.

Equilibrium equations will now be described with reference to FIG. 2b. In FIG. 2b, equilibrium about the pivot (220) is established when the net torque is zero, i.e.:

$$T_g + T_u + T_v = 0 \quad (14),$$

where Tg is the unbalanced torque due to the payload (225), and the unbalanced torque produced from spring (201) and (202) are Tu and Tv respectively. The unbalanced torque produced by the weight is the product of the gravitational force due to the payload M, and the shortest distance between the force vector (M=mg) and the point (220):

$$T_g = Mr \cos(\theta) \quad (2).$$

The net torque of spring (201) about (220) is equal to the sum of the torque produced from the compression of the spring due to the arm displacement (230) and the pre-compression of the spring when the arm is horizontal (230: θ=0), and is given by:

$$T_v = K_y e_1 \cos(\theta - a_1)[(l_1^2 + e_1^2)^{1/2} - (l_1^2 - 2e_1 l_1 \sin(\theta) + e_1^2)^{1/2} + K_y \Delta y] \quad (15),$$

where Ky is the spring rate of (201), and Δy is the displacement of the spring from rest when the arm is horizontal and $l_1$ and $l_2$ is the distance between the pivot (220) and a pivot (250) where the springs 201 and 202, respectively, are coupled to the ground (or fixture). The net torque produced from spring (202) is given by:

$$T_u = K_x e_2 \cos(\theta - a_2)[(l_2^2 + e_2^2)^{1/2} - (l_2^2 - 2e_2 l_2 \cos(\theta) + e_2^2)^{1/2}] \quad (16),$$

where Kx is the spring rate of (202). If $l_1 \gg e_1$ and $l_2 \gg e_2$, then equation (14) can be reduced to equation (5) or (13) as the directions of the force vectors Fu and Fv become horizontal and vertical respectively in the limit as $l_1, l_2 \to \infty$.

Figure 3:
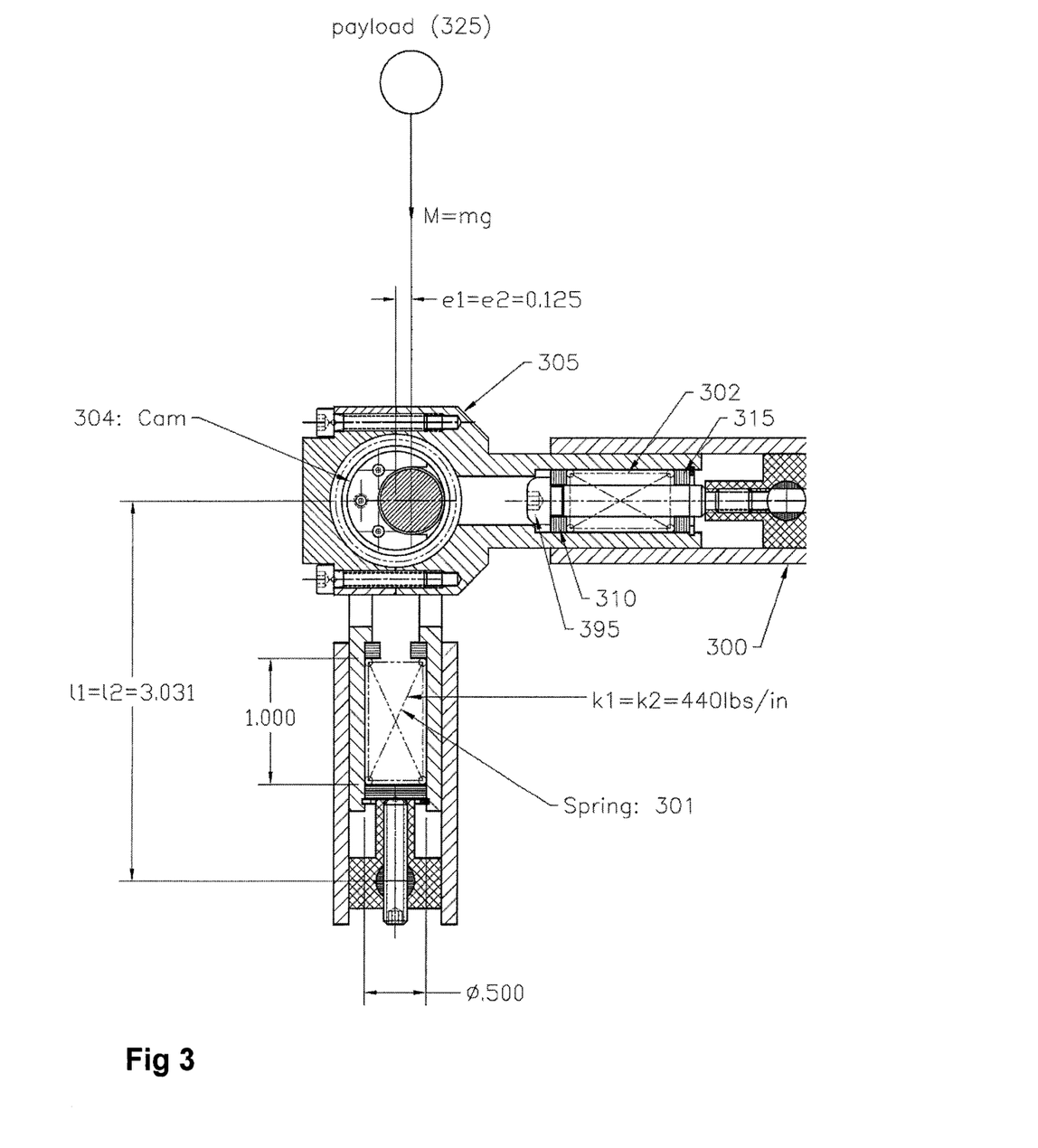
FIG. 3 illustrates a cross-sectional view of a mechanical arm comprising a variant of the spring balance mechanism shown in FIG. 2.

FIG. 3 illustrates a variation to the design presented in FIG. 2. A shoulder bolt (395) was integrated into the previous design to allow compression spring (302) to exert both compressive and tensile loads on cam (304). This assembly was designed to support a payload exerting a maximum torque of 27.5 in-lb. This device can support the payload to a maximum of ±180 degrees from the horizontal rest position of the arm.

When the housing (305) supporting the cam (304) is moved away from the base (300), the spring in turn is trapped between the head of the shoulder bolt (or washer 310) attached to the base (300) and washer 315 (attached to housing 305). Thus, the compression of the spring (302) is converted into a tensile load that is in turn exerted on cam 304.

Alternately, if the housing (305) is displaced toward the base (300), the compression spring (302) is now trapped between washer 310 (now fixed to the housing 305 instead of the shoulder bolt 395 previously described) and the base 300 (and washer 315). Thus, the compression spring is now exerting a compressive load on cam 304.

Figure 4:
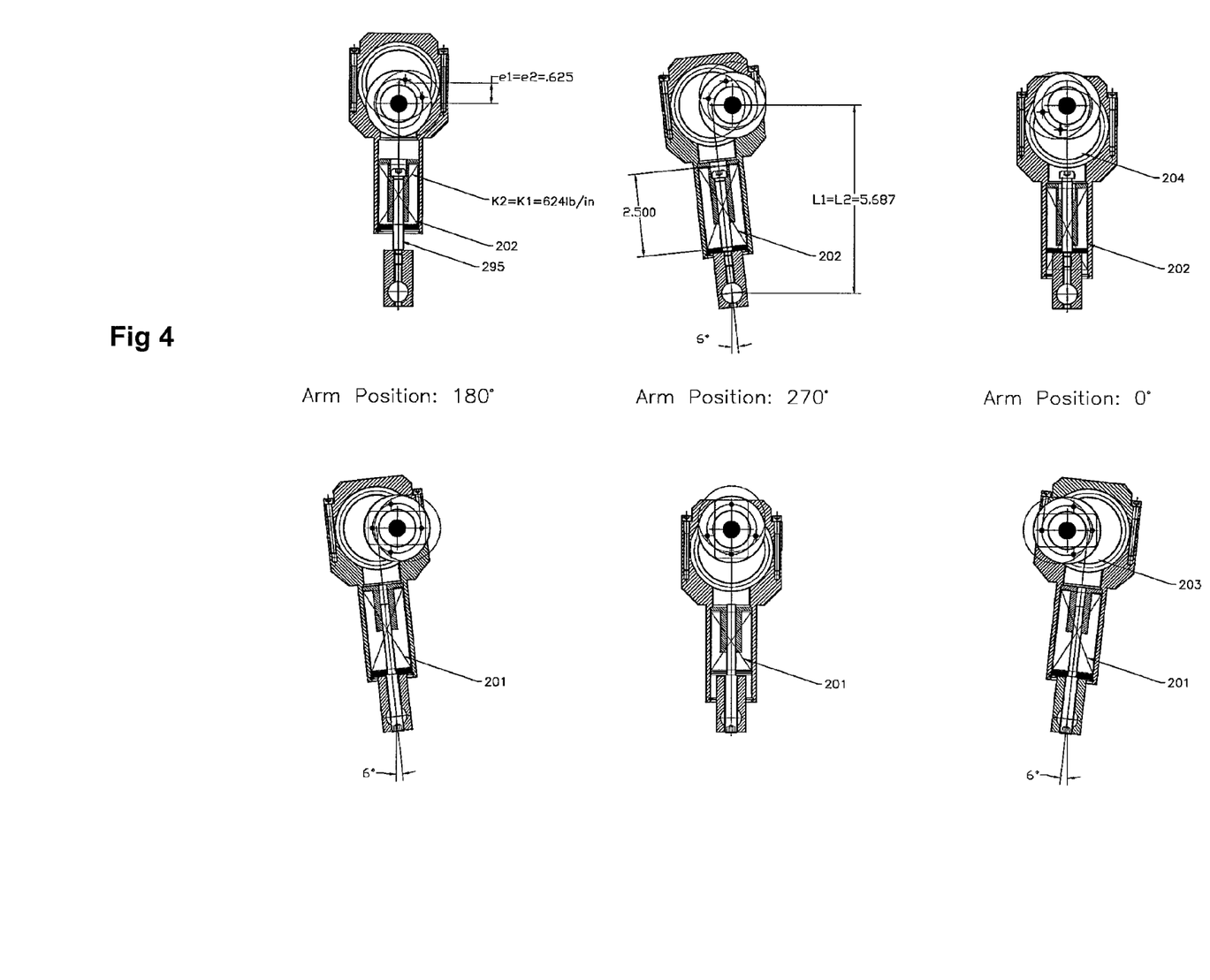
FIG. 4 illustrates the phase relationship between springs and cams in various configurations of mechanical arm rotation.

FIG. 4 illustrates the phase relationship between springs 201 and 202 of the counterbalance assembly shown in FIG. 2 with the addition of a shoulder bolt (295). The shoulder bolt (295) in this design allows the mechanism to apply both compressive and tensile loads to the cam (204). Since the maximum spring compression is not equal to the maximum spring tension, this system will support 97.5% of the payload through its full range of motion. However, if the shoulder bolt were applied to both springs 1 and 2 in the embodiment illustrated in FIG. 2, substantially all of the load but not 100% would be supported through a full 360 degrees of rotation. If the shoulder bolt were applied to both springs 101 and 102 in the embodiment illustrated in FIG. 1a or 1b, substantially all of the load, and up to 100% would be supported through a full 360 degrees of rotation. As '$l_1$' and '$l_2$' approach infinity then the embodiment shown in FIG. 2 becomes equivalent to FIG. 1a or 1b.

FIG. 4 shows a side view of the springs 201 and 202 illustrating the phase relationship between each spring-cam pair for various arm rotations, with rotational positions stated in relation to a Cartesian coordinate system with 0 degree corresponding to positive X axis. This device was designed to support a payload exerting a maximum torque of 200 in-lb:

Arm at 180 degrees (left column): In this orientation, the preload of spring (201: bottom left) is set to exert a torque to balance the payload. The spring (202) does not exert an unbalanced torque in this rotational position.

Arm at 270 degrees (center column): Spring (201: bottom center) does not exert an unbalanced torque in this configuration. Spring (202: top center) is relaxed and does not exert an unbalanced torque to the arm. Since the payload is directly over the pivot, the system is in equilibrium.

Arm at 0 degrees (right column): In this arm rotational position, the preload of spring (201: bottom right) is set exert a torque to balance the payload. The spring (202) does not exert an unbalanced torque in this arm position.

Figure 5:
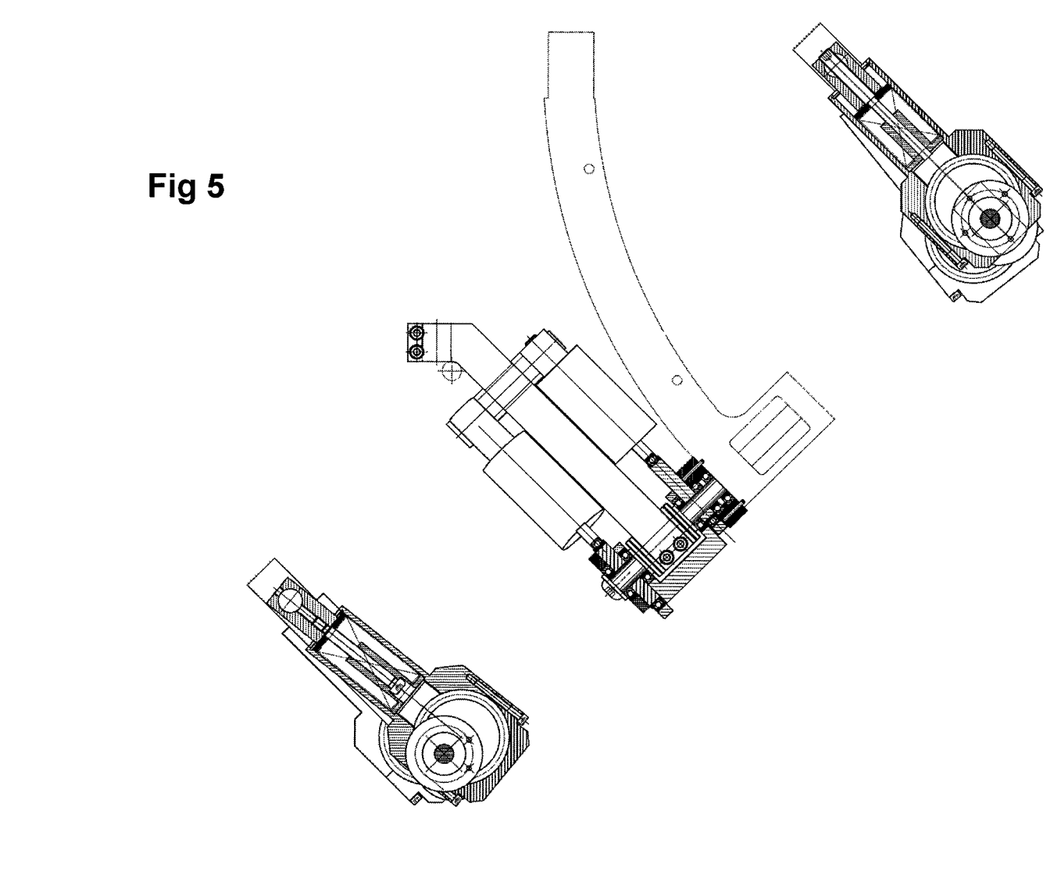
FIG. 5 illustrates a variant to the design presented in FIG. 3.

FIG. 5: illustrates an alternate variation to the design presented in FIG. 3. The spring cam pair(s) illustrated in FIG. 3 were rotated to align both springs in a vertical orientation. However, the relationship between the cam and corresponding spring is still maintained. This design modification supports 97.5% of the load to a maximum of ±90 degrees from its rest position. The rest position of the arm is in the vertical position.

While the Figures show counterbalance assemblies for a joint of a mechanical arm where the assembly comprises two or three springs, the skilled person having the benefit of reviewing the Figures will recognize that the counterbalance assemblies need not be restricted to spring balance mechanisms and will further recognize equivalent counterbalance assemblies.

While springs have been used in the Figures it will be recognized that any force generating device may be used in the counterbalance assembly described herein. A force generating device refers to any structure or device which provides resistance to compressive or tensile forces in response to linear deflection imposed thereon. More specifically, any structure or device that exhibits resistance to linear compression or tension along a longitudinal axis thereof may be useful as a force generating device. Thus, a force generating device includes a longitudinal axis along which linear forces shall be imposed as a result of rotational movement of a mechanical arm. The force generating device interacts with a cam to converts rotational movement of the arm into linear deflection of the force generating device. An example of a force generating device is a spring-like device. A spring-like device is any device or structure that acts like a compression or tension spring in providing resistance to a linear compression and/or tension along a longitudinal axis. An example of a spring-like device is a unit of rubber or other resilient material, or a hydraulic or pneumatic pressurized cylinder any one of which may be used in an equivalent manner to a compression or tension spring by providing resistance to a linear force along a longitudinal axis. Another example of a spring-like device is a spring, such as a compression spring or a tension spring. Compression springs is an example of a low cost force generating device that may be utilized to provide a simplified arrangement within the counterbalance assembly. A compression spring includes a longitudinal axis along which linear compressive forces may be imposed as a result of rotational movement of a mechanical arm. Examples of compression springs include relatively standard die springs as commonly available in the industry. The exact number and size of such springs used in the counterbalance assembly described herein can vary depending upon the counterbalance torque desired, the size of the robotic arm involved, and the like, as will be recognized by the skilled person. The force generating device may be adjustable such that the resistive force provided by the force generating device may be increased or decreased to allow for variation in mechanical arms.

A force generating device will interact with at least one cam in the counterbalance assemblies described herein. A cam is a general term pertaining to a component that rotates or reciprocates to create a prescribed motion in an interacting element, which is often termed the follower. In the context of the counterbalance assembly described herein, a cam may be any structure or device that is set relative to a pivot of a joint, to exert a variable motion on an interacting portion of a force generating device as a function of the rotation of the joint. More specifically, a cam refers to any structure or device that can convert rotational movement of a mechanical arm into a linear movement parallel to a longitudinal axis of a force generating device. A cam is typically set eccentrically relative to a pivot of a joint of the mechanical arm. A cam may be mounted within the circumference of a joint. Alternatively, a cam need not be mounted entirely within the circumference of a joint, and may readily be set outside the circumference of a joint where full rotation is unnecessary or where physical collision or interference of mechanical components is not a concern, for example as may be the case for large industrial robotic arms. One example of a cam is an eccentric bearing. Another example of a cam is a lever extending from the joint that can interact with a force generating device. Cams can be varied shape so as impart a desired linear deflection of the force generating device.

Any technique for achieving an interaction of a cam to its follower known in the art may be used to achieve interaction of a force generating device and a cam in the counterbalance assembly described herein. The Figures show various alternatives of a spring interacting with a cam. For example, FIGS. 1*d*-1*g* show various alternatives of a spring abutting a cam. As another example, FIG. 2 shows a spring hingedly coupled to an eccentric bearing. As yet another example, FIGS. 1*a*-1*c* show a spring coupled to a cam through a yoke. Each of the examples described in the Figures may be used to achieve an interaction between a force generating device and a cam. Still other forms of coupling using slots, pegs or other techniques known in the art can be used to achieve the interaction of a force generating device and a cam. Interaction as used herein contemplates a force generating device abutting or engaging a cam, and a force generating device being linked or coupled to a cam.

The counterbalance assembly has been structurally shown in the Figures using at least two springs with each spring interacting with at least one cam that is mounted eccentrically relative to a pivot of a joint of a mechanical arm. Functionally, the spring/cam relationships can be divided into first and second groups. The purpose of each group is to generate torque. The torque generated by the first and second groups together allows the counterbalance assembly to maintain an equilibrium of torque exerted on a joint throughout the desired rotation of the joint. The torque provided by the first group is used to counteract the torque exerted by the mechanical arm and its associated payload at a rotational position, typically horizontal, where torque exerted by the arm is greatest. The torque provided by the second group is to counteract the linear change in force exerted by the first group. For example, the linear change in force due to linear displacement of springs in the first group when the arm is above horizontal results in the torque exerted by the mechanical arm being greater than the torque exerted by spring/cam pairs in the first group causing the arm to drift back to horizontal. In contrast, the linear change in force due to linear displacement of springs in the first group when the arm is below horizontal results in the torque exerted by the mechanical arm being less than the torque exerted by spring/cam pairs in the first group causing the arm to drift back to horizontal. The torque provided by the second group can maintain equilibrium when the arm is below and above the horizontal. Thus, the torque provided by the second group compensates for the first group to maintain the arm in positions other than the horizontal. The horizontal is the rest position or datum.

Using the specific example shown in FIG. 2 for illustration only, the purpose of spring 201 is to offset for the weight of the payload. To account for its weight, the initial compression of the spring is set with an adjustment screw (for example, item 275, FIG. 2) such that the torque exerted by the spring through the cam is equal to the counter torque resulting from the weight of the payload. The purpose of the second spring is to offset for the linear change in force with compression of the first spring.

For example, the pre-compression load of spring 201 may be set with the arm in a rotational position, typically horizontal, where the arm exerts its greatest torque. Thus, the torque exerted by spring 201 maintains the system in equilibrium with the arm in the horizontal position. This arm position is the datum or rest position. When the arm is displaced from its horizontal position when with the pre-compression load of spring 201 set, the lever will return to its initial rest position (horizontal) without spring 202 present due to change in force exerted by the spring 201 due to linear displacement of the spring. With spring 202 in place, when the arm is displaced from the horizontal, the change in force applied by spring 201 is counteracted by spring 202. The result is the lever will not return to its initial equilibrium position defined by spring 201. With the addition of spring 202, its equilibrium position is no longer related to orientation (230) of the lever/arm.

Counterbalance assemblies described herein may maintain equilibrium of torque for an unlimited degree of rotation. Torque equilibrium may be maintained for arm rotations greater than 1 degree, 45 degrees, 90 degrees, 135 degrees, 180 degrees, 225 degrees, 270 degrees, 315 degrees, 360 degrees, and even greater, in both positive and negative directions.

Counterbalance assemblies described herein may be used for one or more than one joint in a mechanical arm.

The following relationship as described with reference to FIG. 1b holds true for the counterbalance assemblies shown throughout the Figures. Pre-compression of a first spring to counteract torque of a mechanical arm is set for an arm position which exerts its greatest torque, ie horizontal in FIG. 1b. With the arm in this position, the line between the pivot (120) and the center of eccentric cam (103) is substantially perpendicular to the longitudinal axis of spring 101. At this same arm position, the line between the pivot (120) and the center of eccentric cam (104) is substantially parallel to the longitudinal axis of spring 102. In certain examples, with the arm in this position, the line between the pivot (120) and the center of eccentric cam (103) is perpendicular to the longitudinal axis of spring 101, and the line between the pivot (120) and the center of eccentric cam (104) is substantially parallel to the longitudinal axis of spring 102.

Counterbalance assemblies, for example spring balance assemblies, described herein may be used in conjunction with further components as desired to aid in the orientation of mechanical arms, for example, without limitation, brakes for locking a hinged arm, encoders for measuring rotational angles of a hinged coupling, counterweights and/or other balances to offset the mass of the system, computer controlled actuators for automating actuation of a hinged coupling. Further components that may be incorporated into the mechanical arm will be apparent to the skilled person, and suitable combinations of optional components will also be apparent depending on the particular mechanical arm and the particular use of the mechanical arm.

As one example of an optional component, a counterweight may be mounted to the arm to offset the mass of a payload and/or mass of one or more elements of an articulated arm. Although the counterbalance mechanism described herein can eliminate the need for counterweights, counterweights may, if desired, be used in conjunction to offset the mass of the system.

As yet another example of an optional component, a braking mechanism may be mounted within the mechanical arm to inhibit or stop motion of arm elements relative to each other.

As still another example of an optional component, the mechanical arm may be equipped with motors (not shown), for example servo motors that may be controlled by a computer to automate the motion of various linkage elements. The counterbalance mechanism described herein reduces the force required by motors to actuate the mechanical arm.

As another example of an optional component, in embodiments where springs are used in a counterbalance assembly the compression or tension of one or more springs is adjustable.

Still further optional features will be apparent to the skilled person.

The spring balance mechanism may be used in conjunction with many different types of mechanical arms, for example, arms having industrial or medical uses.

Figure 6:
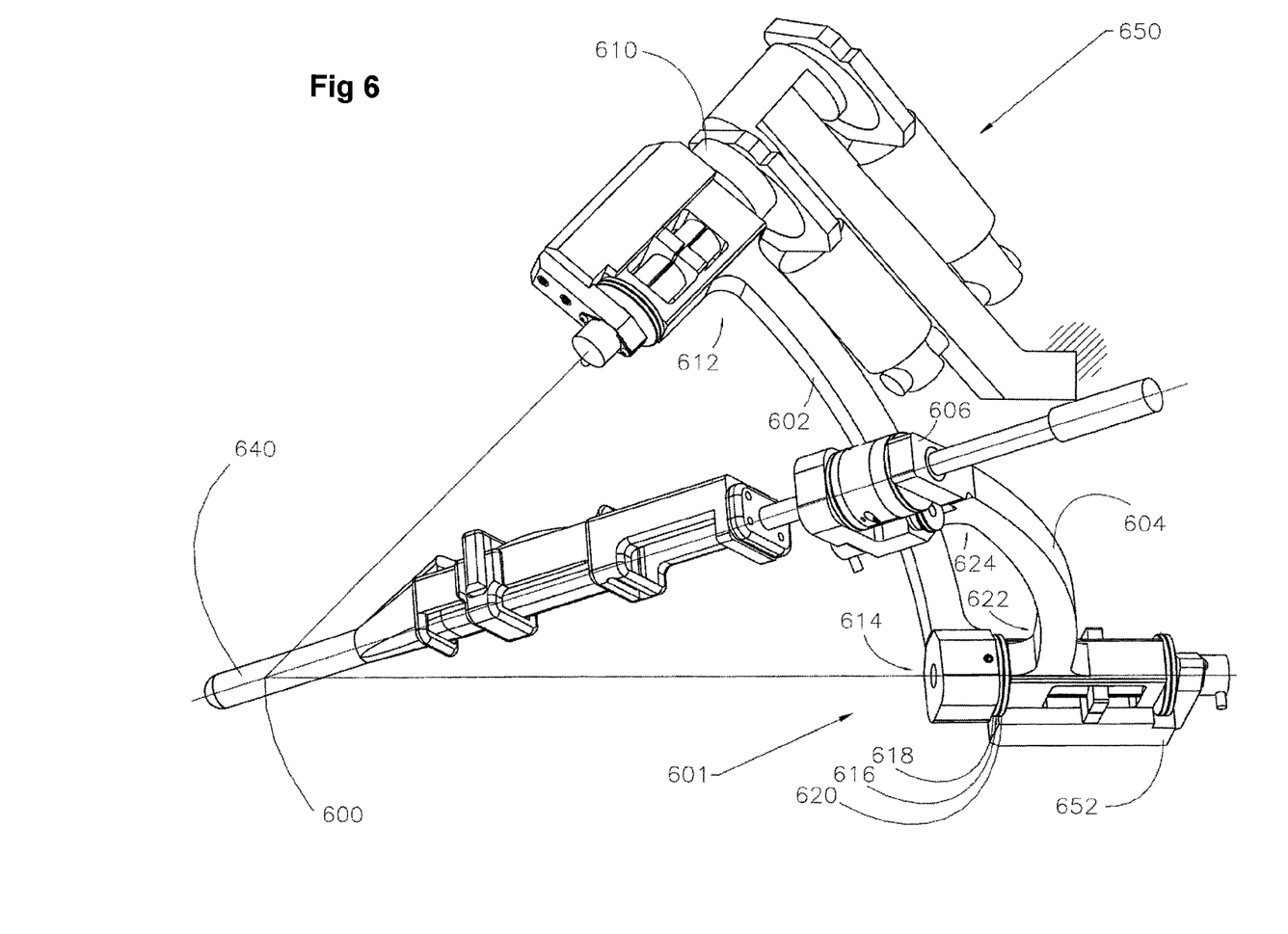
FIG. 6 illustrates an example of a medical guide apparatus that can comprise the spring balance mechanism shown in FIG. 1.

A specific illustrative example of a mechanical arm where the counterbalance assembly may be used is a guide apparatus 601 that may be used for 3D orientation of a medical tool relative to and through a fixed point in space, a remote fulcrum (FIG. 6). The guide apparatus comprises two linkage elements, a crank 602 and a link 604. The crank 602 and the link 604 may be of any size, or shape that allows for the remote fulcrum 600.

The linkage elements may be hingedly coupled to form positioning elements. In FIG. 6 the crank 602 and link 604 both have an arcuate structure having a central angle of about 45 degrees. The crank has a first end 612 and a second end 614. The link also has first and second ends 622, 624. When the guide apparatus is in use the first end 612 of the crank is hingedly coupled to a base or stabilizer. The first end 612 may comprise a full hinged coupling that is attached to a member that is rigidly fixed to the base or ground arm.

Alternatively, the first end 612 may comprise a portion of a hinged coupling 610 with the remainder of the hinged coupling being provided by the base or stabilizer. The second end 614 of the crank forms a hinged coupling 616 with the first end 622 of the link. The second end 614 of the crank comprises a portion 618 of the hinged coupling 616, while the first end 622 of the link comprises the remaining portion 620 of the hinged coupling 616. The second end 624 of the link is coupled to a tool holder 606. The tool holder may be in the form of an adaptable cradle for securing a shaft 632 that may be used to actuate a medical tool 640. The spring balance assembly 650 is provided for the joint between first end 612 and the base or ground arm. A counterweight 652 is provided to offset the weight of the payload. However, if desired counterweight 652 may be replaced with a spring balance assembly.

The above-described embodiments are intended to be examples and alterations and modifications may be effected thereto, by those of skill in the art, without departing from the scope of the invention which is defined by the claims appended hereto.

What is claimed is:

1. A counterbalance assembly for a rotatable mechanical arm comprising:
   a first force generating device interacting with an associated first cam; and
   a second force generating device interacting with an associated second cam, wherein:
   the first and second cams are fixed eccentrically relative to a pivot of a joint about which said mechanical arm rotates, said first force generating device and said second force generating device are offset by 90 degrees, said first and second force generating device are first and second springs, and the relationship of the first force generating device to the second force generating device and the first cam to the second cam is preserved throughout rotation of the mechanical arm.

2. The counterbalance assembly of claim 1, wherein compression of the first force generating device is adjustable.

3. The counterbalance assembly of claim 2, wherein compression of the first force generating device is adjustable such that the torque exerted by the first force generating device and associated first cam offsets torque exerted by the mechanical arm about the joint, when the mechanical arm is in a position to exert its greatest torque about the joint.

4. The counterbalance assembly of claim 1, wherein compression of the second force generating device is adjustable.

5. The counterbalance assembly of claim 1, wherein the longitudinal axis of the first force generating device is substantially perpendicular to a line extending between the pivot and the center of the associated first cam, and the longitudinal axis of the second force generating device is substantially parallel to a line extending between the pivot and the center of the associated second cam, when the mechanical arm is in a position to exert its greatest torque about the joint.

6. The counterbalance assembly of claim 1, wherein the first force generating device applies a compressive load to the associated first cam.

7. The counterbalance assembly of claim 1, wherein the second force generating device applies a compressive load to the associated second cam.

8. The counterbalance assembly of claim 1, wherein the first force generating device applies a compressive load to the associated first cam and the second force generating device applies a compressive load to the associated second cam.

9. The counterbalance assembly of claim 1, wherein the second force generating device applies a compressive load or a tensile load to the associated second cam depending on the rotational position of the mechanical arm.

10. The counterbalance assembly of claim 1, wherein at least one of the first and second cams is set within the circumference of the joint.

11. The counterbalance assembly of claim 1, wherein at least one of the first and second cams is set outside the circumference of the joint.

12. The counterbalance assembly of claim 1, wherein the first force generating device at least offsets the weight of a payload of the mechanical arm, when the mechanical arm is in a position to exert its greatest torque about the joint.

13. The counterbalance assembly of claim 12, wherein the second force generating device offsets the linear change in force of the first force generating device.

14. The counterbalance assembly of claim 1, wherein the first and second force generating devices abut the associated first and second cams, respectively.

15. The counterbalance assembly of claim 1, wherein the first and second force generating devices are coupled to the associated first and second cams, respectively.

16. The counterbalance assembly of claim 1, further comprising a third force generating device in the form of a third spring.

17. The counterbalance assembly of claim 16, wherein the third force generating device interacts with the second cam.

18. The counterbalance assembly of claim 16, wherein the third force generating device interacts with the first cam.

19. The counterbalance assembly of claim 16, further comprising a third cam that interacts with the third force generating device.

20. The counterbalance assembly of claim 16, further comprising a fourth force generating device in the form of a fourth spring.

21. The counterbalance assembly of claim 1, wherein the product of the spring rate of the first spring and the square of the distance between the center of the first cam and the pivot is substantially equal to the product of the spring rate of the second spring and the square of the distance between the center of the second cam and the pivot.

22. The counterbalance assembly of claim 21, wherein the spring rate of the first spring is substantially equal to the spring rate of the second spring.

23. The counterbalance assembly of claim 1, wherein at least one of the first and second springs is a compression spring.

24. The counterbalance assembly of claim 1, wherein at least one of the first and second springs is a tension spring.

25. The counterbalance assembly of claim 1, wherein the mechanical arm is a guide apparatus for supporting a medical tool payload.

26. The counterbalance assembly of claim 25, wherein the guide apparatus comprises a crank, a link hingedly coupled at one end thereof to the crank and a medical tool holder coupled to an opposite end of the link.

27. The counterbalance assembly of claim 26, further comprising a counterweight to offset the weight of the medical tool payload.

* * * * *